United States Patent [19]

Niwa

[11] Patent Number: 5,025,791
[45] Date of Patent: Jun. 25, 1991

[54] PULSE OXIMETER WITH PHYSICAL MOTION SENSOR

[75] Inventor: Minoru Niwa, Nagoya, Japan
[73] Assignee: Colin Electronics Co., Ltd., Japan
[21] Appl. No.: 531,768
[22] Filed: Jun. 1, 1990

[30] Foreign Application Priority Data

Jun. 28, 1989 [JP] Japan ............................ 1-75700[U]

[51] Int. Cl.$^5$ .............................................. A61B 5/14
[52] U.S. Cl. ..................................... 128/670; 128/633; 128/782
[58] Field of Search ............... 128/633, 670, 687, 688, 128/689, 690, 774, 782

[56] References Cited

U.S. PATENT DOCUMENTS

4,202,350  5/1980  Walton ............................... 128/690
4,409,983  10/1983  Albert ............................... 128/690

Primary Examiner—William E. Kamm
Attorney, Agent, or Firm—Oliff & Berridge

[57] ABSTRACT

A reflectance pulse oximeter for detecting pulse synchronous waves is disclosed. The detector includes a sensor or sensors for detecting physical motion of the subject so that readings influenced by subject movement can be eliminated or indicated. One form of motion detector used is an accelerometer employing a spring-supported weight mounted within a cylinder. Accelerations beyond a predetermined value cause the weighted member to complete a circuit against the inside walls of the cylinder. Three accelerometers for detecting acceleration in each of three directions can be utilized. Motion can also be detected by a cubic motion detector having individual reed valves associated with each of six faces. A magnetic ball is movable in a spherical space formed within the cubic body. The magnetic ball operates to actuate only one of the reeds which is at a time. Motion detection can also be accomplished by a combination of the cubic motion detector and one or more accelerometers of the type previously described. A microprocessor control system determines the presence of a pulse synchronous wave from the reflectance detector system and can suppress indication of a pulse synchronous wave occurring simultaneously with motion detection by the motion detecting sensors, which motion is detected for greater than a predetermined period of time. The control system also can include provision for the display of an indication that the displayed pulse synchronous wave occurred during movement of the subject.

7 Claims, 4 Drawing Sheets

PULSE OXIMETER WITH PHYSICAL MOTION SENSOR

BACKGROUND OF THE INVENTION

1. Field of the Invention

The present invention relates to an apparatus for detecting a heartbeat synchronous wave which is produced from a living body in synchronization with heartbeat of the living body.

2. Related Art Statement

There is known an apparatus for detecting a heartbeat synchronous wave produced from a living body in synchronization with heartbeat of the living body, through a probe which is adapted to be set on a body portion of the subject. For example, there is a pulse oxymeter for measuring a blood oxygen saturation of a subject, which includes (a) a first device for emitting toward a body portion of the subject a pair of lights having different wavelengths, (b) a second device for detecting the intensity of each of the lights transmitted through, or reflected from, the body portion and generating a photoelectric pulse wave signal representative of the detected intensities of the lights, and (c) a probe which is set on the body portion and which supports the first and second devices. The magnitude of the photoelectric pulse wave signal varies in synchronization with arterial pulsation (or heartbeat) of the subject, and the pulse oxymeter determines a blood oxygen saturation of the subject based on each pulse of the photoelectric pulse wave. In addition, there is a pulse wave detecting apparatus for detecting a pressure pulse wave produced from an arterial vessel of a subject in synchronization with heartbeat of the subject, through a probe which is set on a body portion of the subject and which supports a pressure sensor adapted to be pressed against an underlying arterial vessel to detect the pressure pulse wave. The pressure pulse wave can be used for determining a blood pressure of the subject.

However, the probe of each of the above-indicated apparatus may be moved relative to a body portion of a subject when a physical motion of the subject occurs. In such cases the heartbeat synchronous wave obtained by the apparatus contains a variation resulting from the relative movement. Meanwhile, in the event that a patient is undergoing a surgical operation, a heartbeat synchronous wave may contain a variation due to an "internal" cause such as use of a surgical knife or administration of a drug, in addition to the variation due to an "external" cause such as the above-indicated relative movement between the probe and the subject's body. Conventionally it has been considerably difficult for a doctor or a nurse to distinguish the variation due to the physical motion of the patient from the variation due to other causes, on the obtained heartbeat synchronous wave. Thus, the conventional apparatus suffer from the problem of providing an inappropriate heartbeat synchronous wave containing variations due to physical motions of a subject in addition to variations due to other causes, or the problem of providing blood oxygen saturation readings or blood pressure readings which are determined based on the inappropriate wave.

SUMMARY OF THE INVENTION

It is therefore an object of the present invention to provide a heartbeat synchronous wave detecting apparatus which is capable of reliably detecting a physical motion of a subject which results in a variation of the heartbeat synchronous wave detected thereby.

The above object has been achieved by the present invention, which provides an apparatus for detecting a heartbeat synchronous wave produced from a subject in synchronization with heartbeat of the subject, the apparatus comprising (1) a probe which is adapted to be set on a body portion of the subject, (2) first sensor means for detecting the heartbeat synchronous wave produced from the subject, the first sensor means being supported by the probe; and (3) second sensor means for detecting a physical motion of the subject, the second sensor means being supported by the probe.

The heartbeat synchronous wave detecting apparatus constructed as described above, has the second sensor means for detecting a physical motion of a subject, and the second sensor means is supported by the probe, which is adapted to be set on a body portion of the subject. During detection of the heartbeat synchronous wave the second sensor means detects a physical motion of the subject. Thus, the invention apparatus is capable of directly detecting physical motions of the subject in a reliable manner, in contrast to the conventional indirect manner in which a human being such as a doctor or a nurse distinguishes variations due to physical motions of a subject from variations due to other causes on the obtained heartbeat synchronous wave.

In a preferred embodiment of the present invention, the second sensor means comprises a housing formed of an electrically insulating material and at least one acceleration sensor, each of the at least one acceleration sensor including (a) an electrically conductive cylindrical member fixed at one of axial ends thereof to the housing, (b) an electrically conductive elongate spring fixed at one of longitudinal ends thereof to the housing, the elongate spring extending in an inner cylindrical space of the cylindrical member along an axis of the cylindrical member such that the other longitudinal end of the elongate spring is spaced apart from an inner surface of the cylindrical member, and (c) an electrically conductive weight member fixed on the other longitudinal end of the elongate spring. When the body portion of the subject moves at an acceleration greater than a reference value in a direction perpendicular to the axis of the cylindrical member, the weight member contacts a cylindrical wall of the cylindrical member, thereby permitting an electric current to flow through the each of at least one acceleration sensor, whereby the second sensor means generates an electric signal representative of the physical motion of the subject. The at least one acceleration sensor may comprise three acceleration sensors, the three acceleration sensors being fixed to the housing such that the axes of the cylindrical members of the three acceleration sensors are perpendicular to each other. The reference value is 1 G, for instance.

In another embodiment of the present invention, the second sensor means comprises a position sensor, the position sensor including (i) a cubic body having six outer faces, and an inner spherical space formed therein, (ii) a spherical magnet member accommodated in the spherical space of the cubic body, and (iii) six switch members embedded in the cubic body, each of the six switch members being located outside the spherical space and inside a corresponding one of the six faces of the cubic body, and selectively placed in an ON and an OFF position thereof, a single switch member out of the six switch members being placed in the ON position thereof and the other five switch members being placed in the OFF positions thereof each depending upon a position of the magnet member in the spherical space. When the body portion of the subject moves, the position of the magnet member in the spherical space being changed and consequently the single switch member in the ON position being changed from one switch member to another, whereby the second sensor means generates an electric signal representative of the physical motion of the subject. In a preferred form of the present embodiment, the second sensor means further comprises at least one acceleration sensor constructed as described above.

In yet another embodiment of the present invention, the apparatus further comprising means for discarding, if the second sensor means continues to detect the physical motion of the subject for a time duration longer than a reference value, the heartbeat synchronous wave detected by the first sensor means during the time duration. The reference time is 100 ms, for instance.

In a further embodiment of the present invention, the apparatus further comprises means for commanding, if the second sensor means detects the physical motion of the subject, the first sensor means to cease from detecting the heartbeat synchronous wave for a predetermined time after the detection of the physical motion.

In a still further embodiment of the present invention, the apparatus further comprises a display for indicating the heartbeat synchronous wave detected by the first sensor means, and means for commanding, if the second sensor means detects the physical motion of the subject, the display to indicate the heartbeat synchronous wave together with an indicia indicative of the physical motion detected by the second sensor means. In the case where the present invention is applied to a pulse oxymeter, the pulse oxymeter may be adapted to indicate on a display thereof an indicia indicative of a physical motion of a subject, together with blood oxygen saturation readings determined based on the heartbeat synchronous wave.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which.

DETAILED DESCRIPTION OF THE PREFERRED EMBODIMENTS

Figure 1:
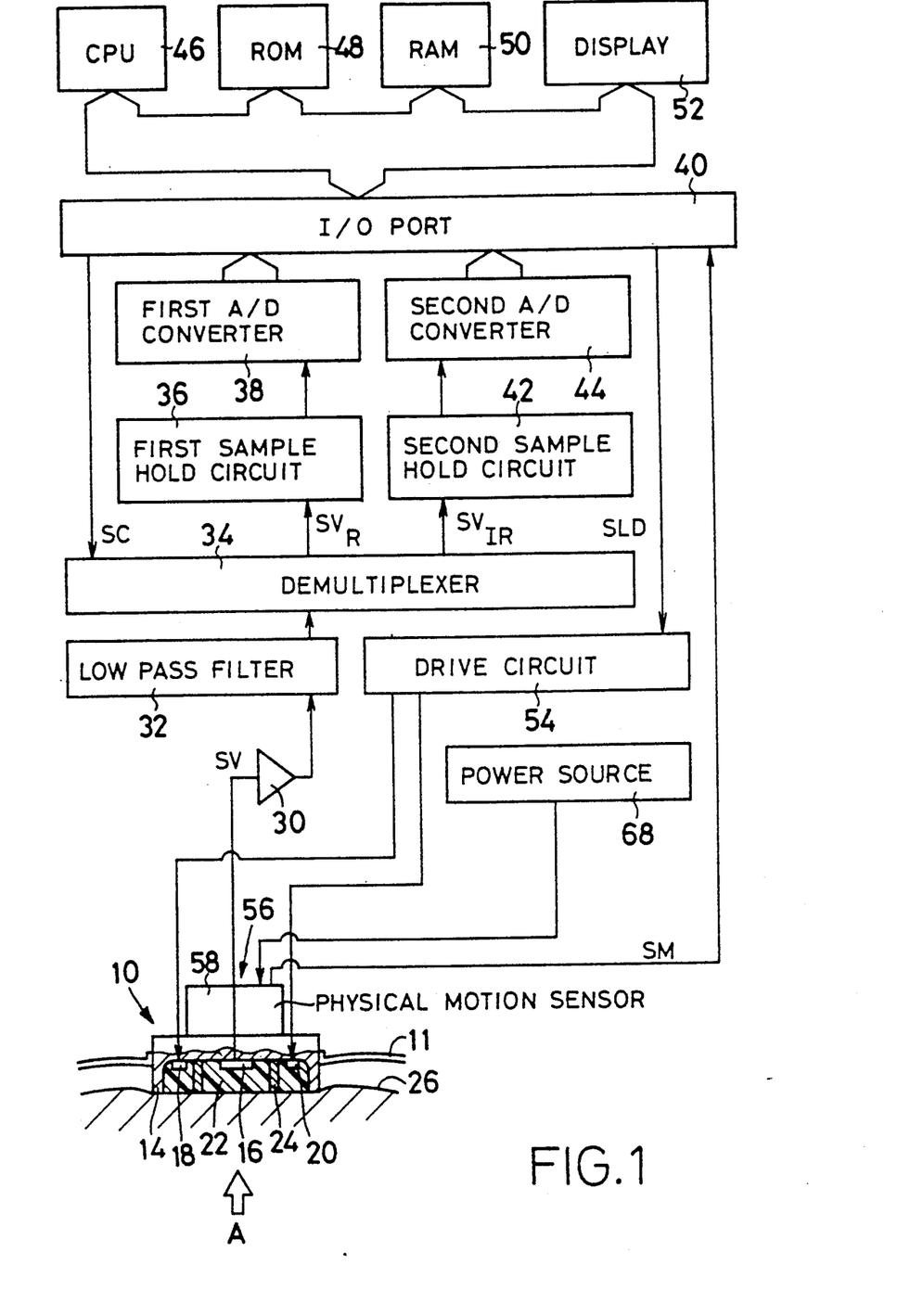
FIG. 1 is a diagrammatic view of a pulse oxymeter embodying the present invention.

Referring first to FIG. 1 there is shown a pulse oxymeter embodying the present invention. In the figure reference numeral 10 designates a probe which is adapted to be set on a body surface 26 of a subject with the help of a band 11 such that the probe 10 closely contacts the body surface 26 with a suitable pressing force. The body surface 26 may be the surface of a finger where the density of peripheral blood vessels including capillaries is comparatively high.

The probe 10 includes a cylindrical support member 14, a light detector 16, a first group of light emitting elements 18, a second group of light emitting elements 20, a transparent resin body 22, and a cylindrical light shading member 24. The cylindrical support 14 has a comparatively shallow bottom, and supports at the center of an inside bottom surface thereof the light detector 16. The light detector 16 is constituted by a photodiode or a phototransistor, for example. As clearly shown in FIG. 2, the first and second groups of light emitting elements 18, 20 are supported on the inside bottom surface of the support 14 such that the eight first light emitting elements 18 and the eight second light emitting elements 20 are alternately disposed around the light detector 16 along a circle whose center coincides with the center of the inside bottom surface of the support 14. Each of the first and second light emitting elements 18, 20 is constituted by an LED (light emitting diode), for example. The transparent resin body 22 fills the shallow inner space of the support 14 and covers the light detector 16 and the light emitting elements 18, 20. The cylindrical light shading member 24 is disposed between the light detector 16 and the light emitting elements 18, 20 in the inner shallow space of the support 14, so that the shading member 24 prevents the lights which are emitted by the light emitting elements 18, 20 and subsequently reflected by the body surface 26, from being detected by the light detector 16. When the probe 10 is set on the body surface 26 of the subject, the transparent body 26 closely contacts the body surface 26.

Figure 2:
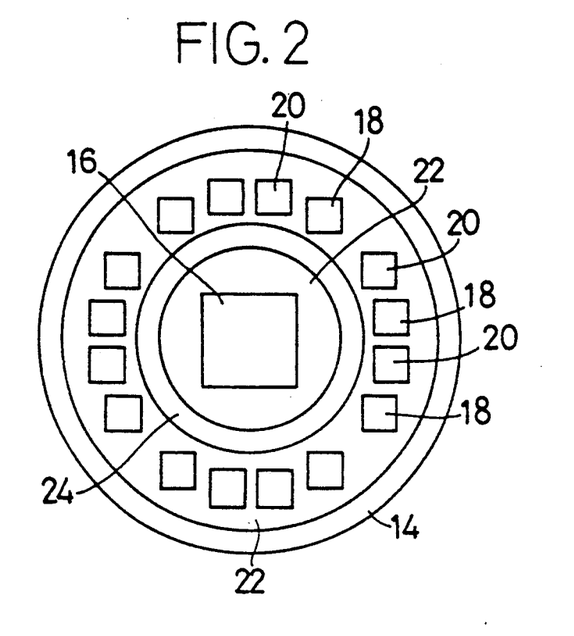
FIG. 2 is an enlarged view of a probe of the pulse oxymeter of FIG. 1 as viewed in a direction indicated at A in FIG. 1.

The eight first light emitting elements 18 are adapted to emit a red light having a wavelength of about 660 mµ, while the eight second light emitting elements 20 are adapted to emit an infrared light having a wavelength of about 800 mµ. Various pairs of lights each pair of which have different wavelengths may be used in place of the 660 mµ and 800 mµ wavelengths lights, so long as one light of the each pair exhibits significantly different absorption factors with respect to hemoglobin and oxygenated hemoglobin, respectively, while the other light exhibits generally same absorption factors with respect to the two sorts of hemoglobins, respectively. The first group of light emitting elements 18 and the second group of light emitting elements 20 alternately and periodically emit red and infrared lights, respectively. A one-time light emission from each group continues a predetermined, very short duration of time. The red and infrared lights emitted by the first and second groups of light emitting elements 18, 20, are reflected from the blood vessels bed lying under the body surface 26, and the reflected red and infrared lights are detected by the common light detector 16.

The light detector 16 generates an electric signal SV whose magnitude corresponds to the detected intensity of each of the reflected red and infrared lights, to a low pass filter 32 via an amplifier 30. The electric signals SV are variable in magnitude because of the pulsation of arterial vessels in the underlying blood vessels bed. Thus, the electric signals SV provide a photoelectric pulse wave signal variable in synchronization with the arterial pulsation of the subject, namely, heartbeat of the subject. In the present embodiment, the photoelectric pulse wave signal serves as a heartbeat synchronous wave produced from a subject in synchronization with heartbeat of the subject. The low pass filter 32 clears the electric signals SV of noise whose frequencies are higher than a frequency of the arterial pulsation, and supplies the cleared electric signals SV to a demultiplexer 34. The demultiplexer 34 is selectively placed in a first and a second position thereof according to a switch signal SC (described below), in synchronization with the alternate and periodic light emissions from the first and second groups of light emitting elements 18, 20. More specifically, when the first group of light emitting elements 18 emit a red light, the demultiplexer 34 is placed in the first position in which the demultiplexer 34 permits an electric signal $SV_R$ representative of the detected intensity of a reflected red light, to be supplied to an I/O (input and output) port 40 via a first sample hold circuit 36 and a first A/D (analog to digital) converter 38. Meanwhile, when the second group of light emitting elements 20 emit an infrared light, the demultiplexer 34 is placed in the second position in which the demultiplexer 34 permits an electric signal $SV_{IR}$ representative of the detected intensity of a reflected infrared light, to be supplied to the I/O port 40 via a second sample hold circuit 42 and a second A/D converter 44. Thus, when the first and second groups of light emitting elements 18, 20 alternately and periodically emit red and infrared lights, respectively, the demultiplexer 34 is correspondingly switched between the first and second positions thereof. The first and second sample hold circuits 36, 42 are adapted to supply the electric signals $SV_R$, $SV_{IR}$ to the first and second A/D converters 38, 44, respectively, such that the sample hold circuits 36, 42 continue to hold the signals $SV_R$, $SV_{IR}$ received in a current cycle until the A/D converters 38, 44 have completed the analog to digital conversions of the signals $SV_R$, $SV_{IR}$ which in the preceding cycle the sample hold circuits 36, 42 have supplied to the converters 38, 44, respectively.

The I/O port 40 is connected via data bus to a CPU (central processing unit) 46, a ROM (read only memory) 48, a RAM (random access memory) 50, and a display 52. The CPU 46 operates for determining a blood oxygen saturation of the subject, by utilizing the temporary storage function of the RAM 50 according to programs pre-stored in the ROM 48. More specifically, the CPU 46 generates a light emit signal SLD to a first drive circuit 54 via the I/O port 40 so that the first and second groups of light emitting elements 18, 20 alternately emit red and infrared lights, respectively, periodically at a predetermined frequency. This frequency is so determined that the present pulse oxymeter can obtain a satisfactory photoelectric pulse wave signal having a sufficiently high density of data points each of which corresponds to an electric signal $SV_R$ or $SV_{IR}$. More specifically, each time the first group of light emitting elements 18 emit a red light, the present pulse oxymeter obtains an electric signal $SV_R$ representative of the intensity of the red light reflected from the blood vessels bed. Similarly, each time the second group of light emitting elements 20 emit an infrared light, the pulse oxymeter obtains an electric signal $SV_{IR}$ representative of the intensity of the infrared light reflected from the blood vessels bed. In synchronization with the alternate and periodic red and infrared lights emissions from the first and second groups of light emitting elements 18, 20, the CPU 46 generates the switch signal SC to the demultiplexer 34 via the I/O port 40 so as to correspondingly place the demultiplexer 34 in the first or second position. Thus, the signals $SV_R$, $SV_{IR}$ are separated from each other by the demultiplexer 34 such that the signals $SV_R$ are sent to the first sample hold circuit 36 while the signals $SV_{IR}$ are sent to the second sample hold circuit 42. Further, the CPU 46 processes the signals supplied from the first and second A/D converters 38, 44 according to programs pre-stored in the ROM 48, and thereby determines an oxygen saturation of the blood flowing through the peripheral blood vessels lying under the body surface 26. The CPU 46 commands the display 52 to indicate the determined blood oxygen saturation.

As shown in FIG. 1 a physical motion sensor 56 is secured to an outer bottom surface (or, upper surface as seen in FIG. 1) of the cylindrical support member 14 of the probe 10. The physical motion sensor 56 serves for detecting a physical motion of the subject, in particular the finger on which the probe 10 is set.

Figure 3:
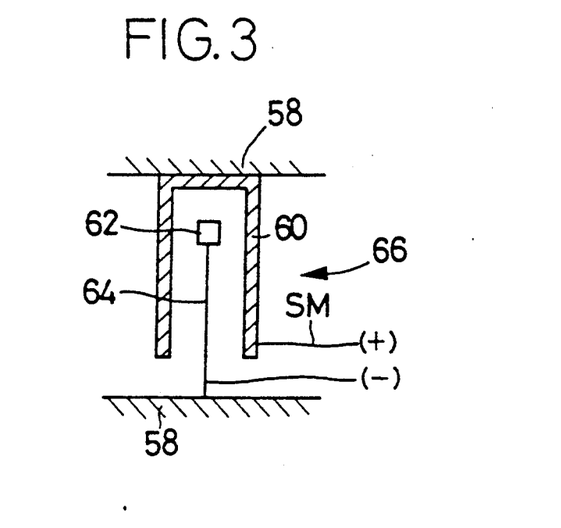
FIG. 3 is a cross-sectional view of an acceleration sensor serving as a physical motion sensor of the pulse oxymeter of FIG. 1.

The physical motion sensor 56 includes a housing 58 formed of an electrically insulating material, and an acceleration sensor 66, as shown in FIG. 3. The acceleration sensor 66 has a cylindrical member 60 formed of a metallic material and fixed at one of axial ends thereof to the housing 58, and an elongate flat spring 64 formed of an electrically conductive material and fixed at one of longitudinal ends thereof to the housing 58. The elongate flat spring 64 extends in an inner cylindrical space of the cylindrical member 60 along an axis of the cylindrical member 60 such that the other longitudinal end of the elongate flat spring 64 is spaced apart from an inner wall surface of the cylindrical member 60. The acceleration sensor 66 further has a weight 62 formed of an electrically conductive material and fixed to the other longitudinal end of the elongate flat spring 64. The weight 62 contacts a cylindrical wall of the cylindrical member 60 when the finger or other body portions of the subject moves in a direction perpendicular to the axis of the cylindrical member 60 and perpendicular to opposite side surfaces of the elongate flat spring 64, at an acceleration greater than a reference value, for example 1 G (gravity). In the present embodiment, the physical motion sensor 56 has three acceleration sensors 66 constructed as described above. The three acceleration sensors 66 are fixed to the housing 58 such that the three axes of the cylindrical members 60 thereof are parallel to an X-axis, an Y-axis and a Z-axis, respectively, which are perpendicular to each other. A power supply applies an electric voltage between the cylindrical member 60 and flat spring 64 of each of the three acceleration sensors 66. When a physical motion of the subject occurs and one or more out of the three weights 62 contact(s) the cylindrical wall(s) of the corresponding cylindrical member(s) 60, an electric current flows through the corresponding acceleration sensor(s) 66. Thus, the physical motion sensor 56 generates a physical motion signal SM representative of the physical motion of the subject, to the CPU 46 via the I/O port 40 as the positive potential falls to ground through sensor 66. The CPU 46 is operated according to the pre-stored programs to discard, if the signal SM is continuously supplied thereto for a time duration longer than a reference value, the photoelectric pulse wave signal (electric signals SV) detected during that time duration. Thus, the display 52 does not indicate blood oxygen saturation readings corresponding to the discarded photoelectric pulse wave signal.

Figure 4:
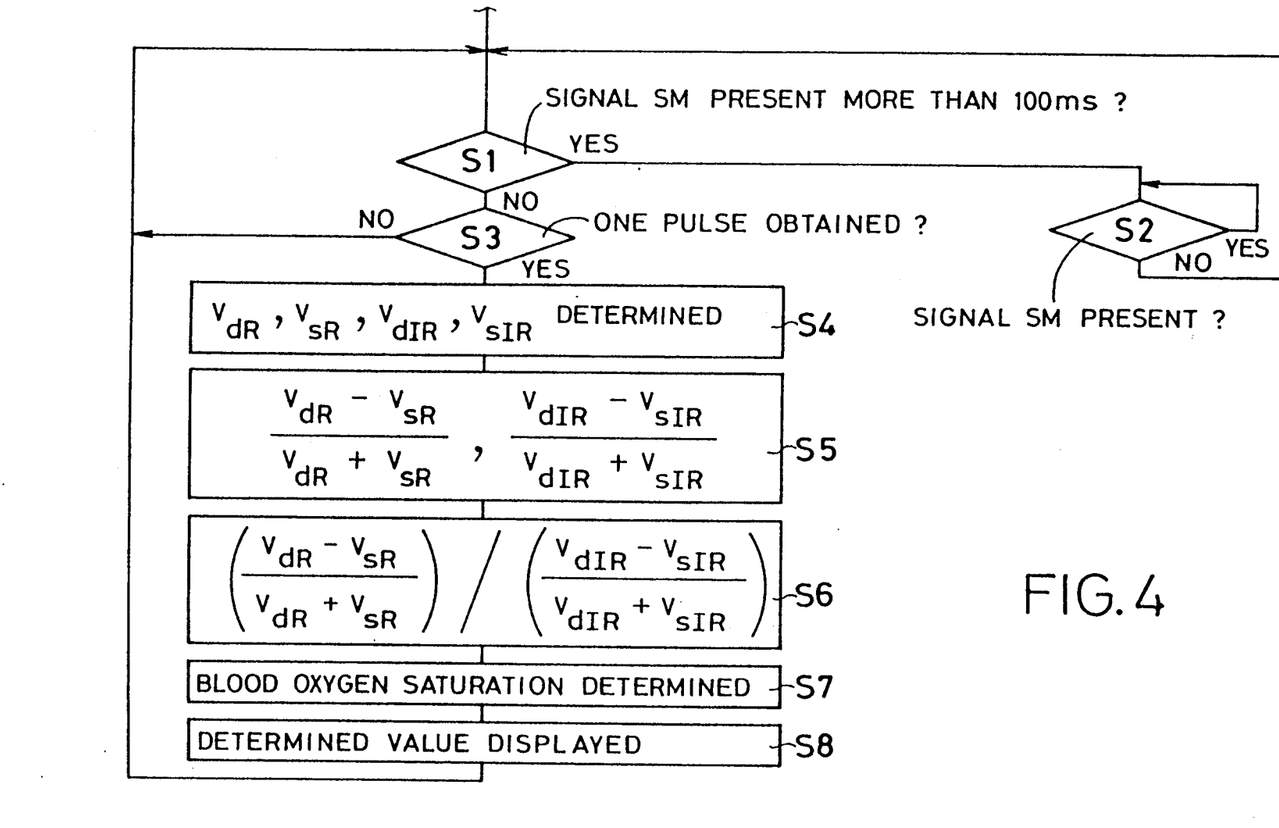
FIG. 4 is a flow chart according to which the pulse oxymeter of FIG. 1 is operated to measure a blood oxygen saturation.

There will be described the operation of the present pulse oxymeter for measuring a blood oxygen saturation of the subject, which operation is carried out according to the flow chart of FIG. 4.

Figure 5:
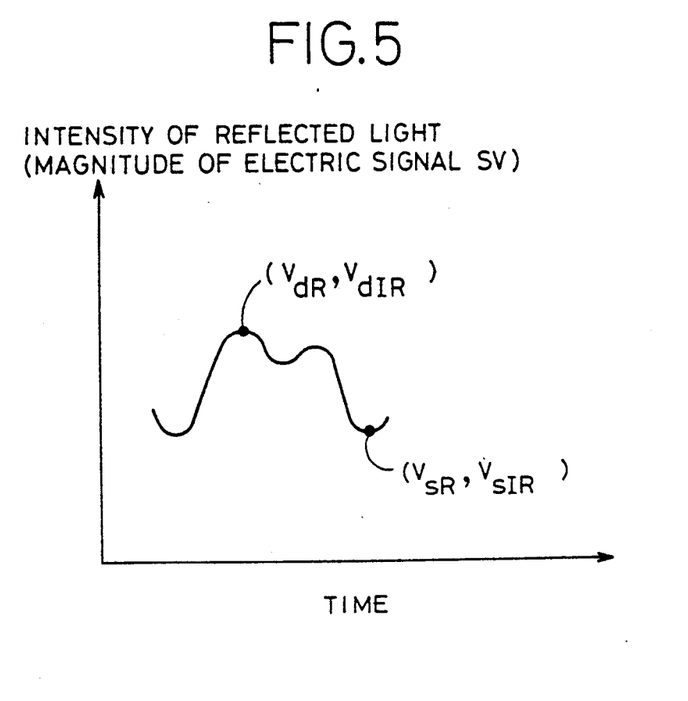
FIG. 5 is a graph indicative of the intensities of a reflected light detected by a light detector of the pulse oxymeter of FIG. 1.

First, the first group of light emitting elements 18 and the second group of light emitting elements 20 are actuated by the drive circuit 54 to alternately and periodically emit red and infrared lights having the different wavelengths, respectively, and the pulse oxymeter successively obtains electric signals $SV_R$ and $SV_{IR}$ representative of the detected intensities of the red and infrared lights, respectively, which have been alternately and periodically emitted by the first and second groups of light emitting elements 18, 20 and subsequently reflected from the underlying blood vessels bed. The control of the CPU 46 begins with Step S1 of the flow chart of FIG. 4. In Step 1 it is judged whether or not the physical motion sensor 56 have continued to generate the physical motion signal SM for a time duration longer than a reference value (for example, 100 ms). In the case where the judgement in Step S1 is affirmative, the control of the CPU 46 proceeds with Step S2 in which it is judged whether or not the physical motion sensor 56 is generating the signal SM, that is, the signal SM is present at the CPU. If the judgement in Step S2 is affirmative, the control of the CPU 46 repeats Step S2, namely remains in Step S2 and waits. Meanwhile, if the judgement in Step S2 is turned negative, the control of the CPU 46 goes back to Step S1. On the other hand, if the judgement in Step S1 is negative, the control of the CPU 46 proceeds with Step S3 in which it is judged whether or not a photoelectric pulse wave signal corresponding to a one-time pulsation of the arterial vessels, namely one pulse of the photoelectric pulse wave signal, has been obtained while the signal SM is not present at the CPU 46. In other words, it is judged whether or not the data points or signals $SV_R$, $SV_{IR}$ sufficient to provide one pulse of the pulse wave signal have been collected while the physical motion sensor 56 does not generate the signal SM. If the judgement in Step S3 is negative, the control of the CPU 46 remains in Step S3 and waits. Meanwhile, if the judgement in Step S3 is turned affirmative, the control of the CPU 46 proceeds with Step S4 in which the CPU 46 determines an upper peak value $V_{dR}$ and a lower peak value $V_{sR}$ of the above-indicated one pulse corresponding to the read light, and an upper peak value $V_{dIR}$ and a lower peak value $V_{sIR}$ of the above-indicated one pulse corresponding to the infrared light. The values $V_{dR}$ and $V_{dIR}$ are representative of the intensities of the red and infrared lights, respectively, which have been reflected from the body surface 26 when the heart of the subject dilates in a diastolic period. Meanwhile, the values $V_{sR}$ and $V_{sIR}$ are representative of the intensities of the reflected red and infrared lights, respectively, which have been reflected from the body surface 26 when the heart of the subject constricts in a systolic period. In FIG. 5 there is shown a graph indicating a single waveform of a photoelectric pulse wave signal representative of the variation in intensity of the reflected red or infrared light. The amplitude of the pulse wave signal reflects a fraction of the red or infrared light which have been absorbed by the arterial vessels (namely, arterial blood flowing therethrough), and therefore an oxygen saturation of the arterial blood.

Step S4 is followed by Step S5 in which the CPU 46 calculates values $(V_{dR}-V_{sR})$, $(V_{dR}+V_{sR})$, $(V_{dIR}-V_{sIR})$, and $(V_{dIR}+V_{sIR})$ based on the upper and lower peak values determined in Step S4, and further calculates the following ratios A and B. Utilization of the ratios A, B ensures that the oxygen saturation readings are free from various influences such as the used intensities of the light emitting elements 18, 20, the specific properties of the light detector 16, the light absorbing characteristics of the skin pigmentation or color of the subject, and the light diffusing and/or absorbing characteristics of the blood vessels bed (these characteristics may vary depending upon the wavelengths of the used lights). Step S5 is followed by Step S6 in which the following ratio A/B is calculated.

$$A = (V_{dR} - V_{sR})/(V_{dR} + V_{sR})$$

$$B = (V_{dIR} - V_{sIR})/(V_{dIR} + V_{sIR})$$

$$A/B = \frac{(V_{dR} - V_{sR})/(V_{dR} + V_{sR})}{(V_{dIR} - V_{sIR})/(V_{dIR} + V_{sIR})}$$

Step S6 is followed by Step S7 in which the CPU 46 determines an actual blood oxygen saturation based on the value A/B obtained in Step S6, according to a predetermined relationship between value A/B and blood oxygen saturation. Subsequently the control of the CPU 46 proceeds with Step S8 in which the CPU 46 commands the display 52 to indicate the determined blood oxygen saturation value. Thereafter the control of the CPU 46 goes back to Step S1 and then the following steps. Thus, each time a one-pulse photoelectric signal is obtained, the pulse oxymeter determines a blood oxygen saturation and indicates the value, whereby blood oxygen saturation values are continuously indicated on the display 52.

As is apparent from the foregoing description, in the present embodiment the physical motion sensor 56 is mounted on the probe 10 which is adapted to be set on the body surface 26 of a subject. Thus, during monitoring of blood oxygen saturation of the subject, the present pulse oxymeter is capable of directly detecting a physical motion of the subject. This direct detection of physical motions of the subject is a more reliable art than the conventional indirect manner in which a human being such as a doctor or a nurse finds variations due to physical motions of a subject on the obtained blood oxygen saturation readings (or obtained photoelectric signal waveform) which contain variations due to not only the external causes such as the physical motions but also the internal causes such as use of a surgical knife or administration of a drug.

In addition, in the present embodiment the physical motion sensor 56 includes the three acceleration sensors 66 positioned along the X-axis, Y-axis and Z-axis, respectively. Thus, the physical motion sensor 56 is capable of reliably detecting the physical motions of the subject in various directions.

Moreover, in the present embodiment, only when the physical motion sensor 56 continues to generate the signal SM to the CPU 46 for a time duration longer than 100 ms, for instance, the CPU 46 discards the photoelectric pulse wave detected during that time duration and does not provide blood oxygen saturation readings.

Thus, the present pulse oxymeter has not only the advantage that the pulse oxymeter prevents determination of a blood oxygen saturation value based on an inappropriate photoelectric pulse wave signal detected during that time duration, but also the advantage that the pulse oxymeter does not cease from monitoring the blood oxygen saturation upon detection of a physical motion lasting a time duration shorter than 100 ms.

While in the illustrated embodiment the pulse oxymeter is adapted to discard the photoelectric pulse wave signal detected during a physical motion of a subject, it is possible to adapt the pulse oxymeter to determine a blood oxygen saturation value based on the photoelectric pulse wave signal detected during the physical motion, and simultaneously indicate on the display 52 that the value has been obtained during the physical motion, for example by shadowing the value or indicating the value together with an indicia indicative of the physical motion. Alternatively, it is possible to adapt the pulse oxymeter to cease, if a physical motion of a subject is detected, from detecting the heartbeat synchronous wave for a predetermined time after the detection of the physical motion.

Figure 6:
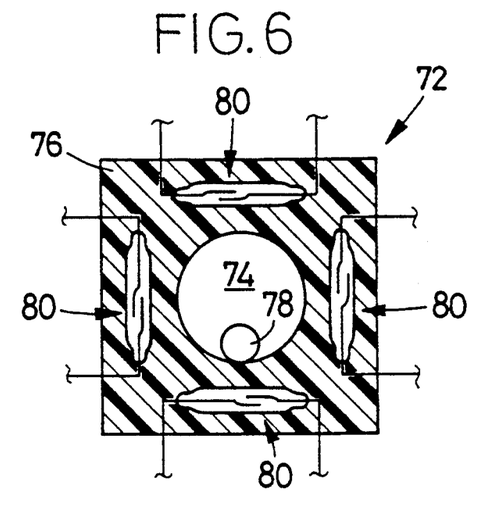
FIG. 6 is a view of another embodiment of the present invention.

Referring next to FIG. 6 there will be described another embodiment of the present invention, in which the physical motion sensor 56 is constituted by a position sensor 72. The position sensor 72 has a cubic body 76 formed of a resin and having an inner spherical space 74 formed therein, and a spherical ferrite magnet 78 accommodated in the spherical space 74 of the cubic body 76. The spherical magnet 78 is displaceable in the spherical space 74 because of gravity, when a body portion of the subject moves. The position sensor 72 further has six well-known reed switches 80 embedded in the cubic body 76 (only the four switches 80 are illustrated in FIG. 6). Each of the six reed switches 80 is located outside the inner spherical space 74 and inside a corresponding one of six faces of the cubic body 76, and selectively placed in an ON and an OFF position thereof. Depending upon a position of the spherical magnet 78 in the spherical space 74, a single reed switch 80 is placed in the ON position thereof and the remaining five reed switches 80 are placed in the OFF positions. When a physical motion of the subject occurs and the position of the spherical magnet 78 in the inner spherical space 74 is changed, the "single" reed switch 80 in the ON position is changed from one reed switch to another, so that the position sensor 72 generates an electric signal representative of the physical motion of the subject. Thus, the position sensor 72 is capable of detecting a comparatively small physical motion of the subject. However, the position sensor 72 is not capable of detecting a comparatively slow physical motion in a vertical or horizontal direction since the spherical magnet 78 and the resin body 78 are not moved relative to each other upon such physical motions. Accordingly it is recommended that the physical motion sensor 56 be constituted by the combination of the position sensor 72, and one or more acceleration sensors 66 shown in FIG. 3. In this case the physical motion sensor 56 is capable of detecting physical motions of a subject in a more reliable manner.

While the illustrated pulse oxymeter is of the reflection type, the present invention may be applicable to a pulse oxymeter of the transmission type which is adapted to utilize the lights transmitted through a body portion of a subject. Moreover, the present invention is applicable to a pulse wave detecting apparatus for detecting a pressure pulse wave produced from a subject in synchronization with heartbeat of the subject, through a probe having a pressure sensitive element which is adapted to be pressed against an arterial vessel of the subject to detect the pressure pulse wave therefrom, or a blood pressure measuring apparatus including such a pulse wave detecting apparatus, for measuring a blood pressure of a subject based on the detected pressure pulse wave. Furthermore, the present invention is applicable to an electrocardiograph for obtaining an electrocardiogram produced in synchronization with heartbeat of a subject, through a probe having electrodes which are adapted to be set on a body surface of the subject. In other words, the term "heartbeat synchronous wave" should be construed as encompassing electrocardiogram waves.

While the present invention has been described in its presently preferred embodiments, it is to be understood that the present invention may be embodied with other changes, modifications and improvements that may occur to those skilled in the art without departing from the scope and spirit of the invention as defined in the appended claims.

What is claimed is:

1. A pulse oximeter of the reflection type, comprising:
   first sensor means including means for emitting two lights having different wavelengths toward a body portion of said subject, and means for detecting the lights reflected from said body portion, said first sensor means producing first signals each of which is representative of a corresponding one of the detected lights;
   second sensor means for detecting a physical motion of said subject, said second sensor means producing a second signal representative of the detected physical motion;
   support means for supporting said first and second sensor means;
   set means for setting said support means supporting said first and second sensor means, on said body portion of said subject; and
   control means for discriminating the first signals produced by said first sensor means when said second signal is produced by said second sensor means, from the first signals produced when said second signal is not produced.

2. The pulse oximeter as set forth in claim 1, wherein said second sensor means comprises a housing formed of an electrically insulating material, and at least one acceleration sensor, each of said at least one acceleration sensor including:
   an electrically conductive cylindrical member including a cylindrical wall and an inner cylindrical space inside said cylindrical wall, said cylindrical wall having an axis and opposite axial ends, said cylindrical wall being fixed at one of said axial ends thereof to said housing;
   an electrically conducive elongate spring member having opposite longitudinal ends, said elongate spring member being fixed at one of said longitudinal ends thereof to said housing, said elongate spring member extending in said inner cylindrical space of said cylindrical member along said axis of said cylindrical member along said axis of said cylindrical wall, the other longitudinal end of said elongate spring member being spaced apart from an inner surface of said cylindrical wall;

an electrically conductive weight member fixed on said other longitudinal end of said elongate spring member; and a power supply applying an electric voltage between said cylindrical member and said elongate spring member, said weight member being displaceable relative to said cylindrical member because of an inertia force exerted on said weight member, and said spring member, so that said weight member contacts said cylindrical wall of said cylindrical member, whereby an electric current flows through said cylindrical member, spring member and weight member, said electric current serving as said second signal representative of said physical motion of said subject.

3. The pulse oximeter as set forth in claim 2, wherein said weight member is displaced relative to said cylindrical member to contact said cylindrical wall, when said body portion of said subject and said cylindrical member thereon move together in a direction perpendicular to said axis of said cylindrical wall as an acceleration greater than 1 G.

4. The pulse oximeter as set forth in claim 1, further comprising means for providing an indication of time, said control means determining an oxygen saturation of said subject based on said first signals produced by said first sensor means, said control means judging fi said second sensor means continues to produce said second signal for a time duration longer than a reference value, and discarding the first signals produced by said first sensor means during said time duration longer than said reference value.

5. The pulse oximeter as set forth in claim 4, wherein said control means discards the first signals produced by said first sensor means during a time duration longer than 100 ms.

6. The pulse oximeter as set forth in claim 4, further comprising a display for indicating said blood oxygen saturation determined by said control means.

7. The pulse oximeter as set froth in claim 1, wherein said control means judges if said second sensor means detects said physical motion of said subject, and commands said first sensor means to cease from producing said first signals for a predetermined time after the detection of said physical motion.

* * * * *